US00PP23770P3

(12) United States Plant Patent
Van Eechaute

(10) Patent No.: US PP23,770 P3
(45) Date of Patent: Jul. 23, 2013

(54) *HOSTA* PLANT NAMED 'COLOR FESTIVAL'

(50) Latin Name: ***Hosta* sp.**
Varietal Denomination: Color Festival

(75) Inventor: Danny Van Eechaute, Deinze (BE)

(73) Assignee: Heemskerk Vaste Planten, Noordwijk (NL)

( * ) Notice: Subject to any disclaimer, the term of this patent is extended or adjusted under 35 U.S.C. 154(b) by 581 days.

(21) Appl. No.: 12/799,275

(22) Filed: Apr. 21, 2010

(65) Prior Publication Data

US 2011/0265231 P1 Oct. 27, 2011

(51) Int. Cl.
*A01H 5/00* (2006.01)

(52) U.S. Cl.
USPC ..... Plt./353

(58) Field of Classification Search
USPC ..... Plt./353
See application file for complete search history.

(56) References Cited

PUBLICATIONS

UPOV ROM GTITM Computer Database, GIT Jouve Retrieval Software Citation for 'Color Festival' Feb. 15, 2010.*
Anonymous. "Plant Files: *Hosta Hostal* 'Color Festival'" available at http://davesgarden.com/guides/pf/go/183383 accessed Oct. 1, 2011.*

* cited by examiner

*Primary Examiner* — Wendy C Haas
(74) *Attorney, Agent, or Firm* — Jondle Plant Sciences Division of Swanson & Bratschun, L.L.C.

(57) ABSTRACT

A new *Hosta* plant named 'Color Festival' particularly distinguished by fluorescent yellow-green streaks between the dark green margins and a light yellow-green central blotch in immature leaves and a yellow central blotch in mature leaves, is disclosed.

2 Drawing Sheets

Genus and species: *Hosta* sp.
Variety denomination: 'Color Festival'.

BACKGROUND OF THE NEW PLANT

The present invention comprises a new and distinct variety of *Hosta*, botanically known as *Hosta* sp. and hereinafter referred to by the variety name 'Color Festival'. The new variety originated in July 2007 in Deinze, Belgium, from a naturally-occurring whole-plant mutation of the parent *Hosta* plant 'Enterprise' (unpatented).

The new variety was first propagated in October 2008 in Rijswijk, The Netherlands via in-vitro propagation, and has been asexually reproduced by in-vitro propagation using meristem tissue culture in Rijswijk, The Netherlands for at least 2 generations. The present invention has been found to retain its distinctive characteristics through successive asexual propagation via in-vitro propagation.

Plant Breeder's Rights for this variety have been applied for in the European Union on Dec. 2, 2009. 'Color Festival' has not been made publicly available or sold more than one year prior to the filing date of this application.

SUMMARY OF THE INVENTION

The following are the most outstanding and distinguishing characteristics of this new variety when grown under normal horticultural practices in Noordwijk, The Netherlands.

1. Fluorescent yellow-green streaks between dark green margins; and
2. A light yellow-green central blotch in immature leaves and a yellow central blotch in mature leaves.

DESCRIPTION OF THE PHOTOGRAPHS

This new *Hosta* plant is illustrated by the accompanying photographs which show the foliage and habit of the plant in full color, the colors shown being as true as can be reasonably obtained by conventional photographic procedures. The photographs are of a 6-month old *Hosta* plant grown in a greenhouse in Noordwijkerhout, The Netherlands.

DESCRIPTION OF THE NEW VARIETY

Figure 1:
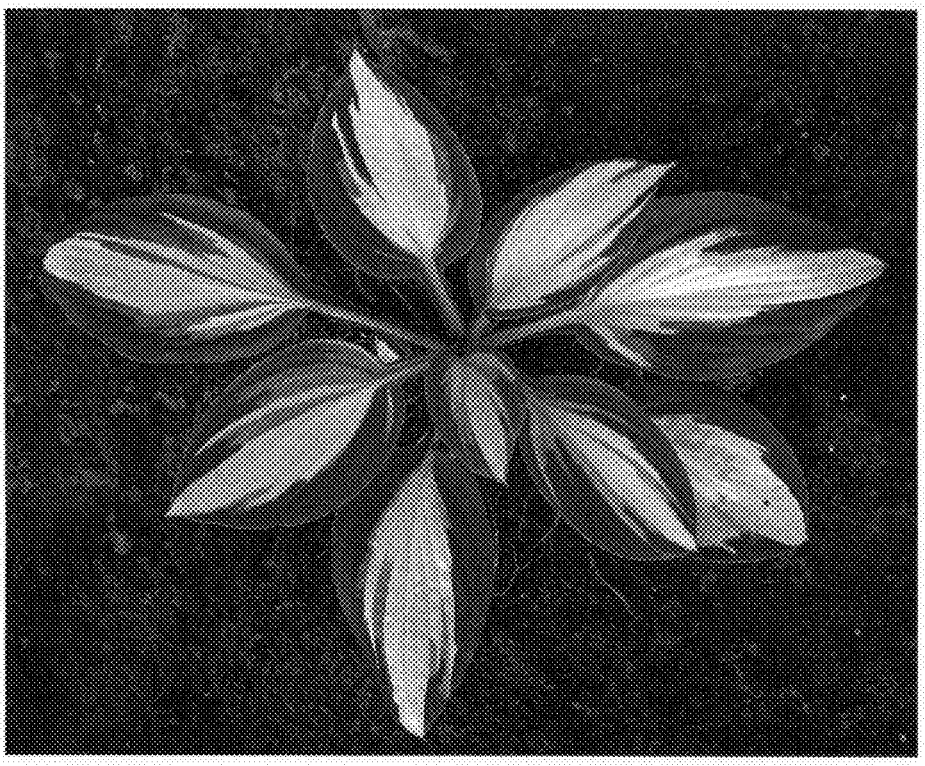
FIG. 1 shows the overall plant habit and foliage.
Figure 2:
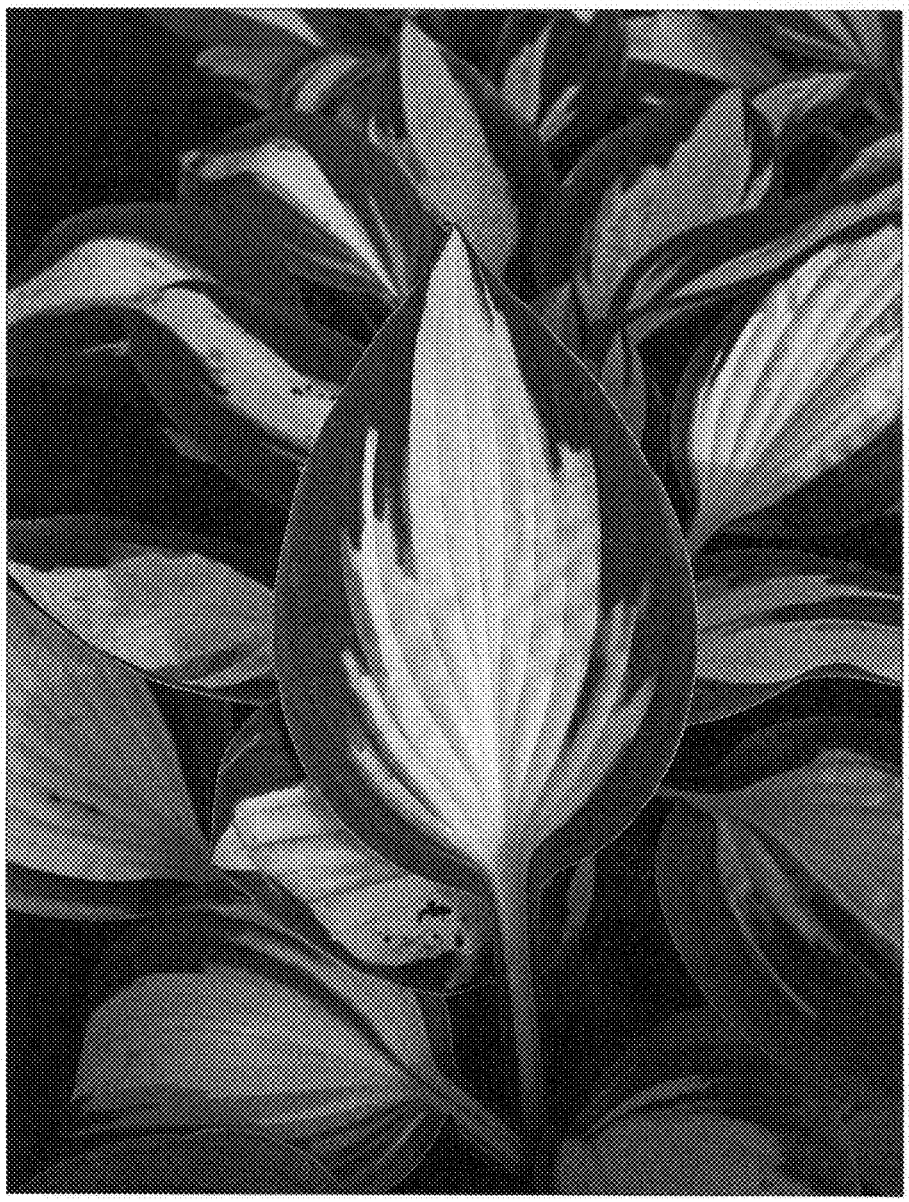
FIG. 2 shows a close-up of a mature leaf.

The following detailed description sets forth the distinctive characteristics of 'Color Festival'. The data which define these characteristics were collected from asexual reproductions carried out in Noordwijkerhout, The Netherlands. The plant history was taken in October 2009 on 6-month old plants grown in 11 cm and larger pots in a glass greenhouse or field grown, in daytime temperatures between 15° C. and 27° C. and nighttime temperatures between 10° C. and 18° C. No growth retardants, photoperiodic treatments, or other cultural or environmental treatments or conditions were used. Observations of the plants were made at a normal light level. Color references are primarily to The R.H.S. Colour Chart of The Royal Horticultural Society of London (R.H.S.) (2007).

DETAILED BOTANICAL DESCRIPTION

Classification:

*Family*.—Liliaceae.
*Botanical*.—*Hosta* sp.
*Denomination*.—'Color Festival'.
*Common name*.—*Hosta*.

Parentage: Naturally occurring whole-plant mutation of *Hosta* 'Enterprise' (unpatented).

Plant:

*Form*.—Herbaceous perennial.

*Shape, habit and vigor*.—Rosette with broad leaves spreading-upright; moderate vigor.

*Height*.—8.7 cm to the top of the foliage.

*Diameter* (*spread*).—33.9 cm.

*Flowering response*.—No flowers observed to date.

*Time to produce a finished plant*.—20 weeks.

*High temperature tolerance*.—Tolerant to at least 32° C.

*Lower temperature tolerance*.—Hardy to at least USDA Zone 5.

Leaves:

*Arrangement and type*.—Basal rosette, single.

*Quantity of leaves* (*per rosette*).—9.

*Durability to stress*.—Moderate to high.

*Shape*.—Ovate, slightly carinate.

*Apex*.—Apiculate.

*Base*.—Attenuate.

*Margin*.—Entire.

*Appearance*.—Slightly glossy, smooth, furrowed on veins.

*Pubescence*.—Absent.

*Size*.—Length: 12.2 cm. Width: 6.7 cm.

*Color* (*immature leaves*).—Upper surface: Between RHS 143B (Green) and RHS 144A (Yellow-green), with a central blotch between RHS 150B (light Yellow-green) and RHS 151D (Yellow-green). Lower surface: RHS 144C (Yellow-green), with a much lighter central blotch of RHS 154C (Yellow-green).

*Color* (*mature leaves*).—Upper surface: Between RHS 138A (Green) and RHS 143B (Green), with a central blotch of RHS 4D (Yellow) with irregular margins between RHS 151C and RHS 151D (Yellow-green). Lower surface: Between RHS 137C (Green) and RHS 137D (Green), with a central blotch of RHS 4D (Yellow).

*Color* (*vein*).—Upper surface: Between RHS 138A (Green) and RHS 143B (Green), with a central blotch of RHS 4D (Yellow), with irregular margins between RHS 151C (Yellow-green) and RHS 151D (Yellow-green). Lower surface: Between RHS 137C (Green) and RHS 137D (Green), with a central blotch of RHS 4D (Yellow).

*Venation pattern*.—Camptodrome.

*Petiole*.—Shape: V-shaped. Length: 8.4 cm. Width: 0.9 cm. Height: 0.4 cm. Color: RHS 154D (Yellow-green), with RHS N137B (Green) margins.

Fruit and seed set: No fruit or seeds observed to date.

Disease and insect resistance: No particular resistance or susceptibility to diseases or insects noted to date.

COMPARISON WITH PARENTAL AND COMMERCIAL VARIETIES

'Color Festival' differs from the parent *Hosta* sp. variety 'Enterprise' (unpatented), in that 'Color Festival' has a light yellow-green central blotch in immature leaves and conspicuous fluorescent yellow-green streaks between the dark green margins and a yellow central blotch in mature leaves, whereas 'Enterprise' has a white central blotch in immature leaves and no streaks between the margins and the central blotch in mature leaves.

'Color Festival' differs from the commercial *Hosta* sp. variety 'Captain Kirk' (unpatented), in that 'Color Festival' has a light yellow-green central blotch in immature leaves and conspicuous fluorescent yellow-green streaks between the dark green margins and a yellow central blotch in mature leaves, whereas 'Captain Kirk' has a yellow central blotch in immature leaves and no streaks between the margin and the central blotch in mature leaves.

I claim:

1. A new and distinct variety of *Hosta* plant named 'Color Festival' as shown and described herein.

* * * * *